United States Patent
Mendez

(10) Patent No.: US 7,137,969 B1
(45) Date of Patent: Nov. 21, 2006

(54) NEURAL TRANSPLANTATION DELIVERY SYSTEM

(75) Inventor: Ivar Mendez, Halifax (CA)

(73) Assignee: Queen Elizabeth II, Health Sciences Centre, Nova Scotia (CA)

( * ) Notice: Subject to any disclaimer, the term of this patent is extended or adjusted under 35 U.S.C. 154(b) by 0 days.

(21) Appl. No.: 10/088,047

(22) PCT Filed: May 26, 2000

(86) PCT No.: PCT/CA00/00614

§ 371 (c)(1),
(2), (4) Date: Jul. 11, 2002

(87) PCT Pub. No.: WO01/17585

PCT Pub. Date: Mar. 15, 2001

(30) Foreign Application Priority Data

Sep. 9, 1999 (CA) .................................. 2282007

(51) Int. Cl.
*A61M 5/00* (2006.01)
(52) U.S. Cl. ....................... 604/187; 604/207; 604/211
(58) Field of Classification Search ............. 604/93.01, 604/181, 186–187, 207–208, 211, 218, 223–224, 604/227, 272, 116–117, 506, 239, 246, 273–274, 604/131, 154–155
See application file for complete search history.

(56) References Cited

U.S. PATENT DOCUMENTS

| 4,415,101 | A | * | 11/1983 | Shapiro et al. | ............. 222/288 |
| 4,518,387 | A | * | 5/1985 | Murphy et al. | ............. 604/187 |
| 4,710,180 | A | * | 12/1987 | Johnson | ..................... 604/239 |
| 6,231,591 | B1 | | 5/2001 | Desai | |
| 6,461,296 | B1 | * | 10/2002 | Desai | ........................ 600/210 |

* cited by examiner

*Primary Examiner*—Catherine S. Williams
(74) *Attorney, Agent, or Firm*—Schmeiser, Olsen & Watts

(57) ABSTRACT

A device and method for neural transplantation in the human brain comprising a microinjector (1), transplantation cannula (2) and bullet guide (16) is disclosed. The microinjector (1) is designed to connect to the proximal end of a syringe barrel (7) and plunger (12) while the transplantation cannula (2) interfaces with the distal end of the syringe barrel (7). In combination, the microinjector (1) and transplantation cannula (2) permit the delivery of multiple cell grafts in a three-dimensional array using a unique spiral technique. The bullet guide (16), which is attachable to a commercially available stereotactic frame, is a multiple channel adapter that functions as a mechanical guiding system for the transplantation cannula (2) and permits plural, spaced deployment of the cannula (2) without adjusting or disturbing the frame.

32 Claims, 9 Drawing Sheets

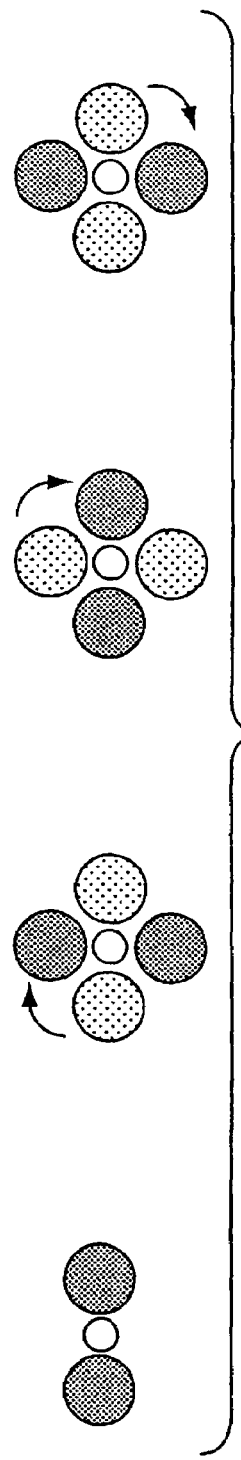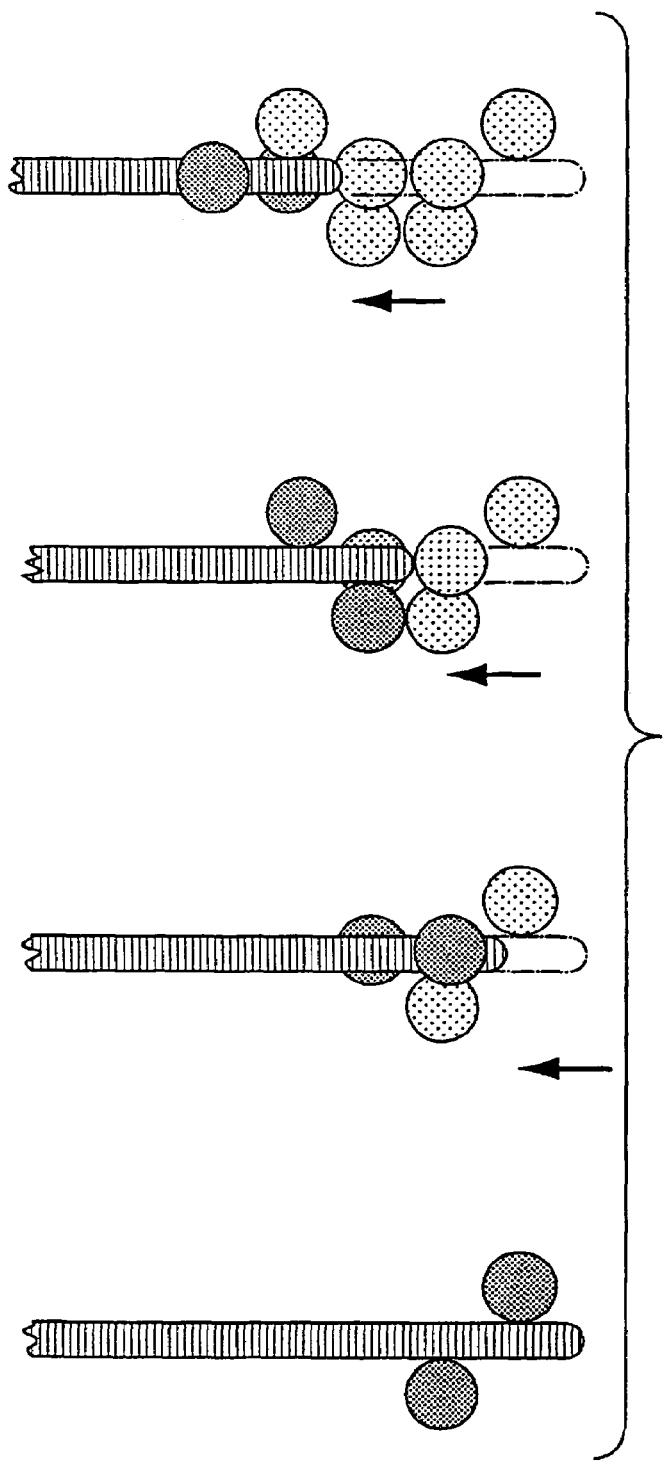
FIG. 6B
FIG. 6A

NEURAL TRANSPLANTATION DELIVERY SYSTEM

FIELD OF INVENTION

The present invention relates to a device and method for neural transplantation in the human brain comprising a microinjector, transplantation cannula and bullet guide. The microinjector and transplantation cannula are adapted to connect to opposite ends of a syringe in a simple manner. The bullet guide, comprised of mutually spaced top and bottom portions, is mounted to a stereotactic frame and functions as a mechanical guiding system for the cannula. In combination, the invention provides a simple, reliable and safe system for delivering and maximizing the number of cell graft deposits to the host brain with minimal trauma using a unique spiral technique.

BACKGROUND OF THE INVENTION

Neural transplantation of fetal ventral mesencephalic (VM) tissue has been studied for the past two decades as a potential surgical strategy for the treatment of Parkinson's disease (PD). Clinical trials in Parkinsonian patients have been conducted in several centres worldwide with more than 200 patients receiving fetal transplants into the striatum (Mehta et al., Can. J. Neurol. Sci., 24, pp. 292–301, 1997; Olanow et al., TINS, 19, pp. 102–109, 1996; Rehncrona et al., Adv. Tech. Stand. Neurosurg., 23, pp. 3–46, 1997; Tabbal et. al. Curr. Opin. Neurol., 11, pp. 341–349, 1998). Survival of the grafts has been documented with positron emission tomography (PET) scanning (Freeman et al., Ann. Neurol., 38, pp. 379–388, 1995; Remy et al., Ann. Neurol., 38, pp. 580–588, 1995; Wenning et al., Ann. Neurol., 42, pp. 95–107, 1997) and postmortem studies (Kordower, et al., N. Engl. J. Med., 332, pp. 1118–1124, 1995). Although the results of these trials have been promising, (Hauser et al., Arch. Neurol., 56, pp. 179–187, 1999; Wenning et al., Ann. Neurol., 42, pp. 95–107, 1997) clinical efficacy has not reached the stage for neural transplantation to become a routine therapeutic procedure for PD. Implantation trauma, which decreases graft survival, and inadequate reinnervation of the host striatum due to suboptimal distribution of graft deposits are considered detrimental factors in achieving optimal clinical efficacy. Decreased implantation trauma and a more complete reinnervation of the dopamine-depleted striatum have been achieved in animal models of PD by decreasing the size of the implantation cannula and increasing the number of deposits of fetal dopaminergic cells (Nikkhah et al., J. Neurosci., 15(5), pp. 3548–3561, 1995; Nikkhah et al., Neurology, 63, pp. 57–72, 1994). These modifications to the implantation technique have produced improvements in host reinnervation and functional recovery in the rodent model of PD (Nikkhah et al., J. Neurosci., 15(5), pp. 3548–3561, 1995; Nikkhah et al., Neurology, 63, pp. 57–72, 1994).

The use of neural transplantation to treat neurological conditions such as PD has the potential to be an important therapeutic strategy in the near future. There is strong evidence of long-term survival of transplanted dopaminergic neurons (Kordower et al., N. Engl. J. Med., 332, pp. 1118–1124, 1995) and clinical results are promising (Hauser et al., Arch. Neurol., 56, pp. 179–187, 1999; Wenning et al, Ann. Neurol., 42, pp. 95–107, 1997). Transplantation in patients with Huntington's disease has also been reported (Kopyov et al., Cell Transplantation for Neurological Disorders, Humana Press, pp. 95–134, 1998) and porcine xenografts are being studied in clinical trials (Deacon et al., Nature Medicine, 3, pp. 350–353, 1997; Isacson et al., al., Nature Medicine, 3, pp. 474–475, 1997). A great deal of experimental work in animals is being conducted for novel cell types as an alternative source to human fetal tissue for neural transplantation. This research may expand the use of reconstructive-strategies in the future (Borlongan et al., Exp. Neurol., 149, pp. 310–321, 1998; Fitoussi et al., Neuroscience, 85, pp. 405–413, 1998; Svendsen et al., Exp. Neurol., 137, pp. 376–388, 1996).

In view of the above comments, neural transplantation holds great promise as a method of achieving a more complete reinnervation of neural tissue and therefore, functional recovery, providing (1) the number of cell deposits to a target site in a subject can be maximized, (2) the distribution of graft deposits can be optimized, and (3) implantation trauma caused by multiple insertions of a transplantation device can be avoided.

Presently, a neural transplantation device and method used for administering neural cells and/or tissue is described by Cunningham in U.S. Pat. No. 5,792,110 wherein the device essentially comprises a guide cannula for penetrating a selected transplant site in a subject to a predetermined depth, and a delivery cannula with a single opening for delivering neural cells and/or tissue to the subject. The guide and delivery cannulas both have an interior lumen and openings at their proximal and distal ends. The delivery cannula, however, has an outer diameter and particular shape that enables it to fit and move within the interior lumen of the guide cannula. Furthermore, the delivery cannula is capable of protruding through the distal end of the guide cannula by way of a flexible distal end portion which enables it to be deflected at a suitable angle from the guide cannula. The method of delivering cell deposits essentially involves advancing the guide cannula into the brain to the transplant site wherein the delivery cannula, which carries the cells, is advanced within the lumen of the guide cannula, and beyond the distal opening of the guide cannula. Cells are deposited along a first extension pathway by advancing the delivery cannula to a distal targeted site and performing a series of injections alternated with incremental retraction of the delivery cannula at predetermined sites along the path. The three dimensional array is essentially achieved by executing several penetrations of the delivery cannula at other distal transplant sites to achieve a similar arrangement of cell deposits along different extension paths located an equidistance from one another.

The delivery device and method described by Cunningham possesses a number of certain disadvantages. In particular, because the outside diameter of the guide cannula is relatively large, e.g. 1.07 mm, the insertion of the guide cannula into the brain during standard neural transplant procedures has the potential to cause localized trauma to the tissue and ultimately result in cell death and poor graft integration. Other disadvantages associated with a transplant cannula having a large diameter is a lower precision in graft placement and a lower reliablity in delivery of very small volumes to a selected site in a subject. In addition, the design of this particular transplantation device only allows multiple grafts to be delivered along a single path with each insertion of the delivery cannula. Supplementary grafts at sites which are not along this path, require the delivery cannula to be removed and reinserted along a new path. Although it is desirable to deliver multiple grafts along different paths in a three dimensional configuration, reinsertion of the cannula increases the risk of trauma to the brain of the transplant recipient with each new penetration thereby contributing to low and variable graft survival and functional recovery. Furthermore, because the delivery cannula is deflected at an angle from the guide cannula and causes the delivery cannula to enter the brain tissue in an oblique fashion, this is also potentially harmful to the brain. Another disadvantage of the Cunningham transplantation device is that the shape of the opening at the extreme distal end of the delivery cannula is not blunt and is potentially harmful to the brain. Moreover, the opening of the tip of the delivery cannula has the potential to become obstructed in the course of performing multiple insertions of the delivery cannula, thereby eventually preventing ejection of a cell and/or tissue suspension.

Accordingly, there is a need for a neural transplantation device and method which can precisely deliver a predetermined volume amount of cells and/or tissue to a selected transplant site in a three dimensional configuration without having to perform multiple insertions of the device. Furthermore, such a device and method should minimize tissue damage and provide for increased survival of the cells and functional integration of the graft in the subject.

According to the present invention, there is provided a neural transplantation system, comprising a microinjector, transplantation cannula and bullet guide in combination with a syringe mounted to a stereotactic frame, which affords a simple, reliable and safe system for improved delivery and maximization of the number of cell graft deposits to the host brain with minimal trauma using a unique spiral technique.

SUMMARY OF THE INVENTION

An object of the present invention is to provide a delivery system for neural transplantation grafts, comprising a microinjector and transplantation cannula, which facilitates delivery in a three dimensional configuration at a targeted site within a subject while undertaking a minimal number of penetrations into the host brain.

Another object of the present invention is to provide a delivery system for neural transplantation grafts, comprising a microinjector and transplantation cannula, which permits the precise placement of a predetermined amount of neural cells or tissue to a targeted site in a subject.

Another object of the invention is to provide a delivery system for neural transplantation grafts, comprising a microinjector and transplantation cannula, that can be easily incorporated with a syringe to facilitate reliable and safe neural transplantation of cell grafts to the human brain.

A further object of the invention is to provide a delivery system for neural transplantation grafts, comprising a microinjector and transplantation cannula, which in combination with a syringe, are designed to minimize implantation tissue trauma and maximize the number of graft deposits per injection using a unique spiral technique.

Still another object of the invention is to provide a bullet guide which, when mounted to a stereotactic frame, functions as a mechanical guiding system for the transplantation cannula thereby permitting multiple access of the cannula without adjusting or disturbing the frame.

According to one aspect of the invention there is provided a neural transplantation device for use in combination with a syringe, including a syringe barrel and plunger, comprising:

a microinjector adapted for connection to a proximal end of a syringe barrel and in cooperation with a syringe plunger for effecting incremental depression of the plunger; and a cannula adapted for connection to a distal end of a syringe barrel, said cannula having a single passageway with an open-upper end and a lower end defining a blunt closed tip and having a pair of side port holes that are diametrically opposed and slightly offset to each other near the vicinity of the cannula tip;

whereby upon placement of the cannula at a predetermined targeted neural site, the microinjector is capable of effecting incremental depression of the plunger to result in a metered delivery of the contents of the syringe barrel through the cannula port holes at the targeted site.

A particular embodiment provides a neural transplantation device, characterized in that the microinjector comprises:

a longitudinal hollow cylindrical sleeve extending into a cylindrical barrel of larger diameter at the distal end thereof, said sleeve capable of receiving a syringe plunger;

a guide nut rotatably adjustable within the cylindrical barrel and adapted to cooperate with the proximal end of the syringe barrel; and a driving means rotatably-mounted near the proximal end of the cylindrical-sleeve and adapted to cooperate with the syringe plunger;

whereby operation of the microinjector in combination with the syringe and the cannula allows delivery of an injection such that rotation of the driving means renders a downward axial force to the plunger of the syringe thereby aspirating contents of the syringe barrel through the side port holes of the cannula; while rotation of the guide nut in the opposite direction moves the syringe in an upward axial direction to reposition the cannula; and rotation of the driving means and the guide nut in a repeated manner facilitates sequential delivery of multiple portions of the contents of the syringe barrel along a single trajectory in a three-dimensional spiral array at a predetermined neural injection site. According to another aspect of the invention, there is provided a method of using the neural transplantation device for administering an injection, comprising the steps of:

positioning the syringe plunger in an initial upward position;

positioning the syringe barrel with attached guide nut in an essentially unwound position inside the cylindrical barrel of the sleeve of the microinjector;

rotating the driving means to advance the syringe plunger in a downward axial direction through the syringe barrel thereby aspirating and depositing a portion of the contents of the syringe barrel through the side port holes of the cannula;

rotating the guide nut to effectively withdraw the syringe and cannula in an upward axial direction at a predetermined distance away from a previous neural target site; and repeating steps involving rotating the driving means to deliver a portion of the contents of the syringe barrel and rotating the guide nut to reposition the cannula, thereby resulting in sequential delivery of multiple portions of the contents of the syringe barrel in a three-dimensional spiral array per single trajectory at a predetermined neural target site.

Yet according to another aspect of the invention, there is provided a bullet guide for use in combination with a stereotactic frame which functions as a mechanical guiding system for the neural transplantation cannula, the bullet guide comprising:

a top member comprising a hollow cylindrical element having a closed end with an array of equidistantly spaced holes sized to accommodate the insertion of the cannula; and a bottom member comprising a hollow cylindrical element of the same diameter as the top member but having a longer longitudinal axis; said bottom member being closed at both ends and each end having an array of equidistantly spaced holes sized to accommodate the insertion of the cannula;

characterized in that the top member and bottom member are mounted in spaced coaxial alignment in the stereotactic frame with the respective arrays of holes in mutual alignment to guide deployment of the cannula through an aligned set of said holes to a predetermined cerebral target.

Thus, the present invention affords a microinjector and transplantation cannula adapted and designed for use, for instance, with a 50 μl Hamilton syringe. The Hamilton syringe comprises a syringe barrel, which receives fluid contents, and a rod-like plunger for expelling the fluid contents from the barrel. In the assembled relationship, the microinjector and cannula create a secure and cooperative attachment to the extreme proximal and distal ends, respectively, of a Hamilton syringe, such that all the components are coaxially aligned to one another.

The microinjector essentially comprises a longitudinal cylindrical sleeve which is threaded on its exterior surface and extends abruptly into a plunger guide at its distal end that has a larger diameter than the sleeve. The exterior surface of the plunger guide is uniform and its internal diameter is sized to fit and cooperate with the peripheral shoulder of the barrel of a syringe. The inner wall of the plunger guide is threaded to match and interface with a guide nut which is adjustably rotated inside the barrel. The guide nut is a small hollow cylindrical spool with a collar at its extreme distal end that acts as a lower boundary stop to limit its position inside the plunger guide when fully wound. In turn, the guide nut is designed to securely interface with the syringe immediately beneath the peripheral shoulder located at the extreme proximal end of the barrel. Accordingly, attaching the guide nut to the barrel converts the syringe to an adjustably rotated device that can easily be wound inside the plunger guide. Therefore, rotating the guide nut in either a clockwise or counter-clockwise direction simultaneously rotates the syringe in the same direction. Depending on the direction of rotation, this operation ultimately translates into either an upward or downward vertical-movement of the syringe. Therefore, the vertical distance in which the syringe moves by rotation of the guide nut is a function of the length and diameter of the plunger guide and guide nut.

Mounted at the proximal end of the cylindrical sleeve is a driving means comprising a threaded drive nut engaged with a threaded plunger driver which are both adjustably rotated in either a clockwise or counter-clockwise direction. As a result of their connection, rotating one element moves the other element simultaneously. The plunger driver is engaged with the proximal end of a syringe plunger such that when the driver is rotated, the movement of the plunger is controlled in either an upward or downward direction along a longitudinal axis parallel to the syringe. Therefore, during neural transplantation, rotation of the plunger driver results in delivery of a desired volume of cell suspension contained within the syringe barrel. The microinjector is advantageously manufactured from acetal nylon and ionized aluminum.

The transplantation cannula of the present invention advantageously comprises a long narrow needle provided with a standard Luer lock at its proximal end. The Luer lock allows the cannula to be readily attached to and in fluid connection with the contents of the syringe, and then easily removed following use. The tip of the cannula at the extreme distal end is closed and blunt and its outer surface is polished and rounded, for instance in a hemispherical shape, to minimize trauma to neural tissue during insertion. Located near the tip of the cannula are a pair of port holes to allow egress of cells during aspiration of the syringe. The port holes are advantageously diametrically opposed and slightly offset to each another. This arrangement minimizes brain trauma, while maximizing cell graft deposits. The use of a pair of holes is important since a larger number of holes would tend to increase the risk of trauma and possible damage to neural tissue. Likewise, the positioning of the holes on opposite sides of the cannula in an offset arrangement is important for obtaining adequate delivery and distribution of cell graft deposits. The transplantation cannula is advantageously manufactured from stainless steel.

The bullet guide, which comprises both a top portion and a bottom portion, is mounted to a stereotactic frame and functions as a mechanical guiding system for the transplantation cannula. The top portion of the bullet guide, being the stop bullet, is a hollow cylindrical tube which is closed at its proximal end and circumscribed by a peripheral collar. The surface of the closed end embodies a square grid, preferably consisting of nine holes equidistantly spaced apart and sized to accommodate the diameter of the transplantation cannula. The bottom portion, being the guide bullet, is a hollow cylindrical tube of similar diameter to the stop bullet but with a longer longitudinal axis. The guide bullet is closed at both the proximal and distal ends and the surface of each end has a square grid identical to the stop bullet to accommodate the insertion of the transplantation cannula. In addition, the guide bullet is circumscribed by a peripheral collar at its extreme proximal end and has an inwardly tapered portion with a flat surface at its extreme distal end. The peripheral collar of each of the guide bullet and stop bullet contains an indexing groove formed of a particular dimension and shape to allow both portions to selectively interface and cooperate with a commercial stereotactic frame when mounted. The positioning of the indexing groove ensures that when the stop bullet and guide bullet are mounted, their grids will be coaxially aligned one above the other thereby allowing the transplantation cannula to be precisely guided and inserted at a predetermined cerebral target. Both the stop bullet and guide bullet are advantageously manufactured from acetal nylon and each component can preferably be disassembled into four separate parts to allow for effective cleaning and sterilization.

Prior to operation of the neural transplantation device, the microinjector, syringe and transplantation cannula are mounted in the stereotactic frame, positioned at a predetermined location and oriented at the cerebral target site using the guide bullet to direct the cannula. The desired cerebral target site is generally identified by a diagnostic imaging technique (e.g. magnetic resonance imaging, computerized tomography, ultrasound, or the like).

During the initial stage of operation, the plunger of the syringe is in a foremost upward position and the syringe barrel with attached guide nut is in an unwound position inside the plunger guide. When an injection is to be administered, the plunger driver is rotated, thereby advancing the syringe plunger in a downward vertical direction through the syringe barrel. A specific volume of the cell suspension is subsequently aspirated and deposited through the port holes of the transplantation cannula at the target site. Prior to making a second injection and deposit of the cell suspension, the guide nut is rotated 90° in a clockwise direction thereby incrementally retracting the syringe and cannula in an upward vertical direction at a predetermined distance away from the first target site. Aspiration and delivery of a second volume of cell suspension is made by repeating the operation involving rotation of the plunger driver. Sequential repetition of the steps involving rotation of the plunger driver and guide nut to deliver the contents of the syringe and reposition the cannula, respectively, allows several injections to be made thereby distributing the cells in a three-dimensional spiral array within the brain tissue. Consequently, control of delivery of the cell suspension, location of the port holes of the transplantation cannula and the distance of syringe movement enable the user to employ the microinjector device with accuracy and precision at a cerebral target site.

Additional cell deposits at different trajectories are made by removing the microinjector device from its operative position, governed by the square grids of the bullet guide, and then reinserting the transplantation cannula of the microinjector through another specified landmark within the grid.

Thus, the invention affords a simple and reliable method to deposit graft material into the brain using a transplantation cannula and microinjector system easily adaptable to any stereotactic frame. The two-hole design of the cannula tip has been validated by animal experiments which demonstrated the ability of the cannula to deliver two distinct graft deposits per injection. This design allows for graft deposits to be placed no more than 2 mm apart from each other. This distance is close enough for the grafts to become confluent since fibre outgrowth has been shown to extend 2 to 7 mm into the host tissue in human transplantations (Kordower et al., n. Engl. J. Med., 332, pp. 1118–1124, 1995). In the grafted rats, the cannula tract facilitated the connection of the two graft deposits. Proper distribution of graft deposits to facilitate confluency in all three dimensions may improve host reinnervation and clinical outcome (Freed et al., N. Engl. J. Med., 327(22), pp. 1549–1555, 1992; Freeman et al., Ann. Neurol., 38, pp. 379–388, 1995).

Implantation trauma is known to be detrimental to graft survival (Nikkah et al., Brain res., 633, pp. 133–143, 1994; Nikkah et al., Neurology, 63, pp. 57–72, 1994) and applicant's animal experiments showed excellent graft survival with no significant trauma to transplanted rat striatum, which is an indication of the atraumatic nature of the cannula design. This observation in the experimental model correlates well with the absence of hemorrhage or tissue damage on the 24 hour post-operative MRI scans of transplanted patients. There was also an increase in fluorodopa uptake on PET imaging after transplantation. At present, the only valid method to assess graft survival in vivo is by measuring fluorodopa with PET scans. Fluorodopa is an analog of levodopa, which is taken over the blood-brain-barrier, decarboxylated and stored in the nigrostriatal dopaminergic terminals. Correlation of graft survival and fluorodopa PET scans has been made by a postmortem examination of a patient transplanted with fetal VM tissue 18 months before death of causes unrelated to the transplant procedure (Kordower et al., N. Engl. J. Med., 332, pp. 1118–1124, 1995).

The cannula is designed to optimize host reinnervation by maximizing the number of deposits per pass. Increasing the density of reinnervation per pass may lead to a reduction in the number of passes through the brain and decrease the chance of hemorrhagic complications. The cannula may be used with cell suspensions that are not completely dissociated and contain "chunks" of fetal VM and no problem has been encountered with the aspiration or delivery of this "chunky" cell preparation. Delivery of solid "cores" of fetal VM have been previously described in the literature using a "double-cannula system" (Breeze et al., Neurosurgery, 36, pp. 1044–1048, 1995).

Accordingly, the present invention provides a simple, safe and reliable neural transplantation delivery system. As neural transplantation evolves and the clinical efficacy of this strategy for the treatment of neurological conditions is established, the ability to deliver viable grafts with minimal trauma may play an important role in neurosurgery.

The experimental and clinical experience with the use of a neural transplantation cannula and microinjector system specifically designed to decrease implantation trauma and maximize the number of graft deposits per injection is also provided. Animal studies conducted using the rat model of PD during the experimental stage of this study demonstrated excellent graft survival with minimal trauma to the brain. Following this experimental stage, the cannula and microinjector system were employed in eight Parkinsonian patients enrolled in the Halifax Neural Transplantation Program who received bilateral putaminal transplants of fetal VM tissue.

BRIEF DESCRIPTION OF THE DRAWINGS

In the following description, the invention will be explained in detail with the aid of the accompanying drawings which illustrate preferred embodiments of the present invention and in which:

FIGS. 6A and 6B illustrate front and top views, respectively, of a sequence of graft deposits using the neural transplantation cannula;

DETAILED DESCRIPTION OF THE PREFERRED EMBODIMENTS

Figure 1:
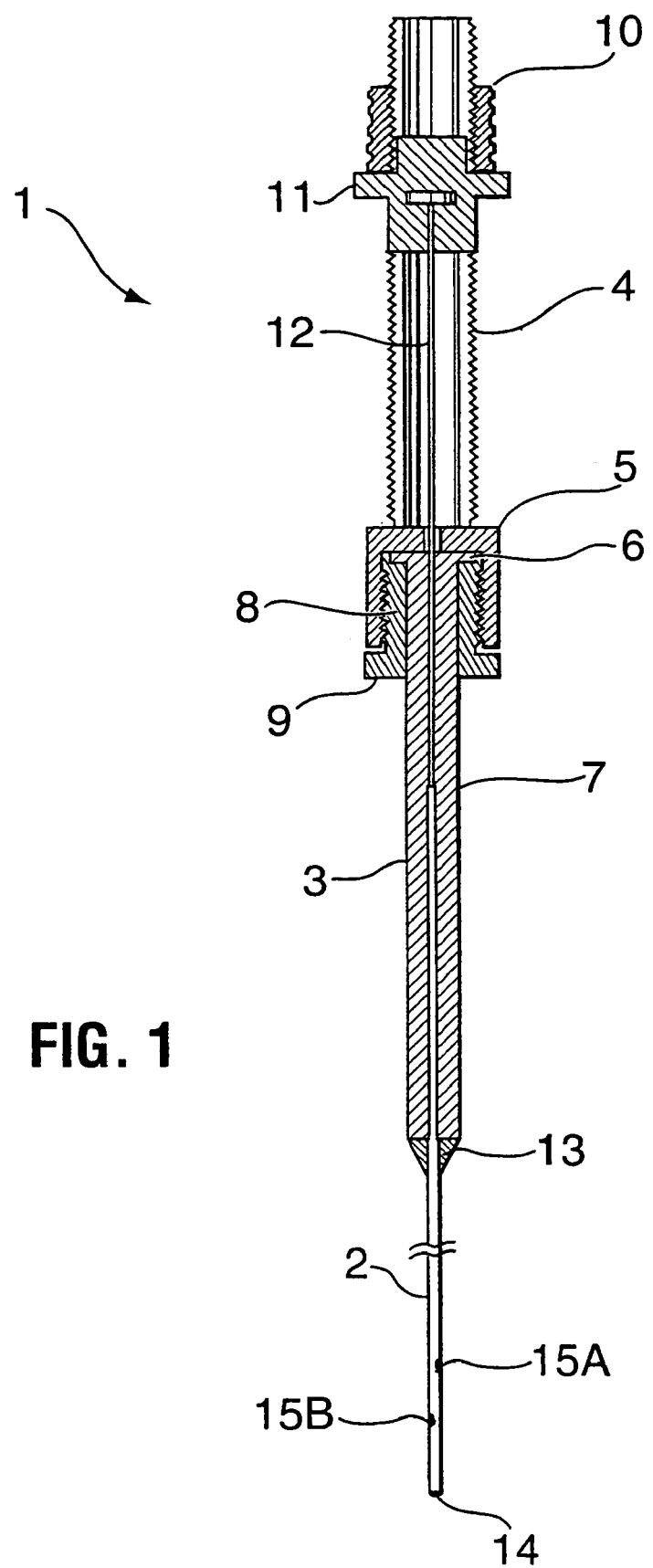
FIG. 1 illustrates a cross-section of a microinjector and neural transplantation cannula fitted to a syringe.

As illustrated in FIG. 1, an embodiment of the present invention affords a microinjector (1) and transplantation cannula (2) adapted and designed for use with a 50 µl Hamilton syringe (3).

The microinjector (1) essentially comprises a longitudinal cylindrical sleeve (4) which is threaded on its exterior surface and extends abruptly into a plunger guide (5) at its distal end that has a larger diameter than the sleeve (4). The exterior surface of the plunger guide (5) is uniform and its internal diameter is sized to fit and cooperate with the peripheral shoulder (6) of the barrel (7) of a Hamilton syringe (3). The inner wall of the plunger guide (5) is threaded to match and interface with a guide nut (8) which is adjustably rotated inside the barrel. The guide nut (8) is a small hollow cylindrical spool with a collar (9) at its extreme distal end that acts as lower boundary stop to limit its position inside the plunger guide (5) when fully wound inside. In turn, the guide nut (8) is designed to securely interface with the Hamilton syringe (3) immediately beneath the peripheral shoulder (6) located at the extreme proximal end of the barrel (7). Accordingly, attaching the guide nut (8) to the barrel (7) coverts the syringe (3) to an adjustably rotated device that can easily be wound inside the plunger guide (5). Therefore, rotating the guide nut (8) in either a clockwise or counter-clockwise direction simultaneously rotates the syringe (3) in the same direction. Depending on the direction of rotation, this operation ultimately translates into either an upward or downward vertical movement of the syringe (3). Therefore, the vertical distance in which the syringe (3) moves by rotation of the guide nut (8) is a function of the length and diameter of the plunger guide (5) and guide nut (8).

Mounted at the proximal end of the cylindrical sleeve (4) is a driving means comprising a threaded drive nut (10) engaged with a threaded plunger driver (11) which are both adjustably rotated in either a clockwise or counter-clockwise direction. As a result of their connection, rotating either the drive nut (10) or plunger driver (11) moves the other element simultaneously. The plunger driver (11) is engaged with the proximal end of a syringe plunger (12) such that when the driver (11) is rotated, the movement of the plunger (12) is controlled in either an upward or downward direction along a longitudinal axis parallel to the syringe (3). Therefore, during neural transplantation, rotation of the plunger driver (11) results in delivery of a desired volume of cell suspension contained within the syringe barrel (7).

Figure 2:
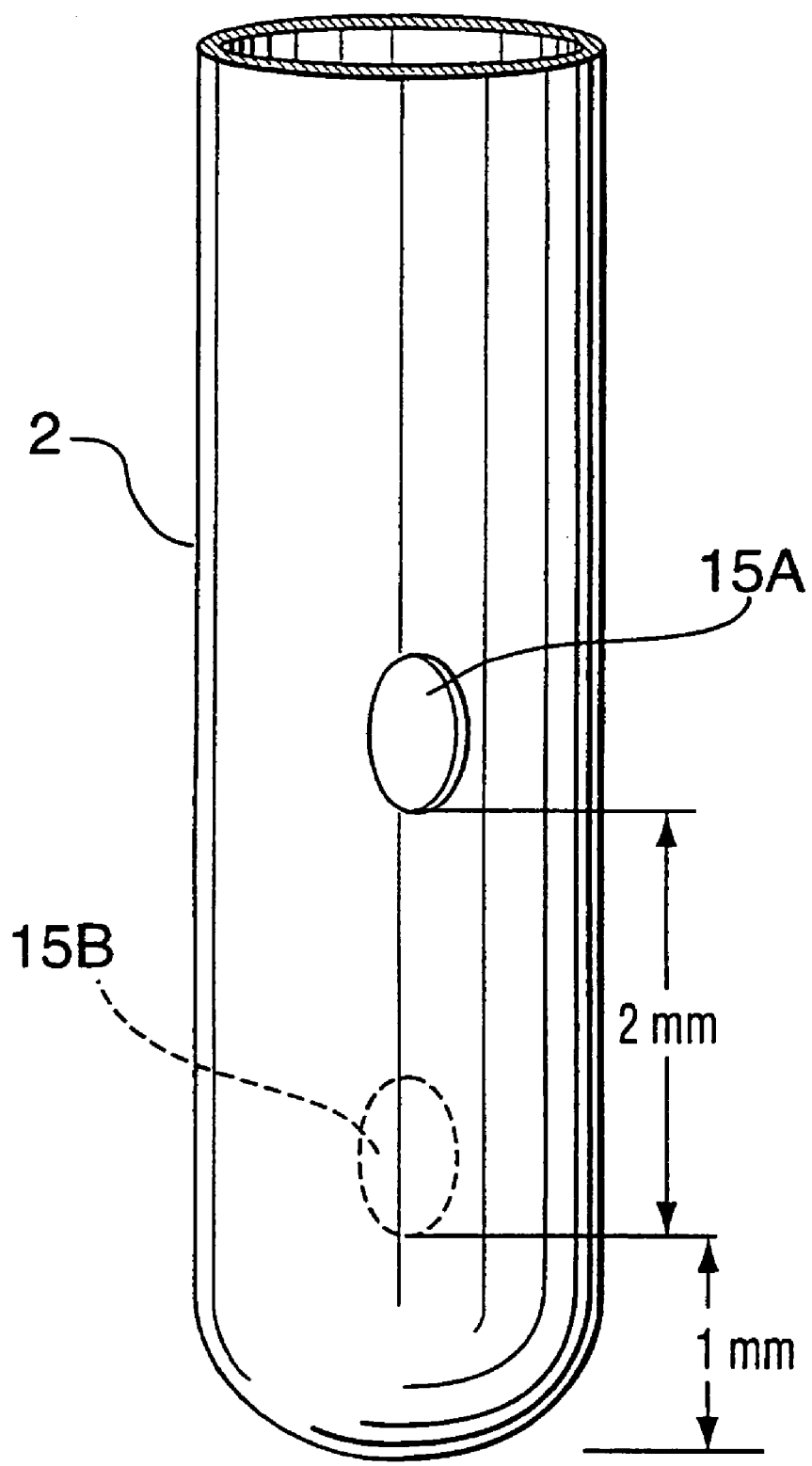
FIG. 2 is an enlarged view of the distal end of the neural transplantation cannula.

The transplantation cannula (2) is a long narrow needle provided with a standard Luer lock (13) at its proximal end. The Luer lock (13) allows the cannula (2) to be readily attached to and in fluid connection with the contents of the syringe (3), and then easily removed-following use. The tip of the cannula (2) at the extreme distal end (14) is closed and its outer surface has been rounded and polished in a semispherical shape to minimize trauma to neural tissue upon insertion. As shown in FIG. 2, located near the tip of the cannula are a pair of holes, (15A) and (15B), to allow egress of cells during aspiration of the syringe (3) and which are diametrically opposed and slightly offset to one another. In the embodiment shown, hole (15B) is located 1.0 mm from the cannula tip (14) and hole (15A) is offset from hole (15B) by a distance of 2.0 mm.

Figure 3:
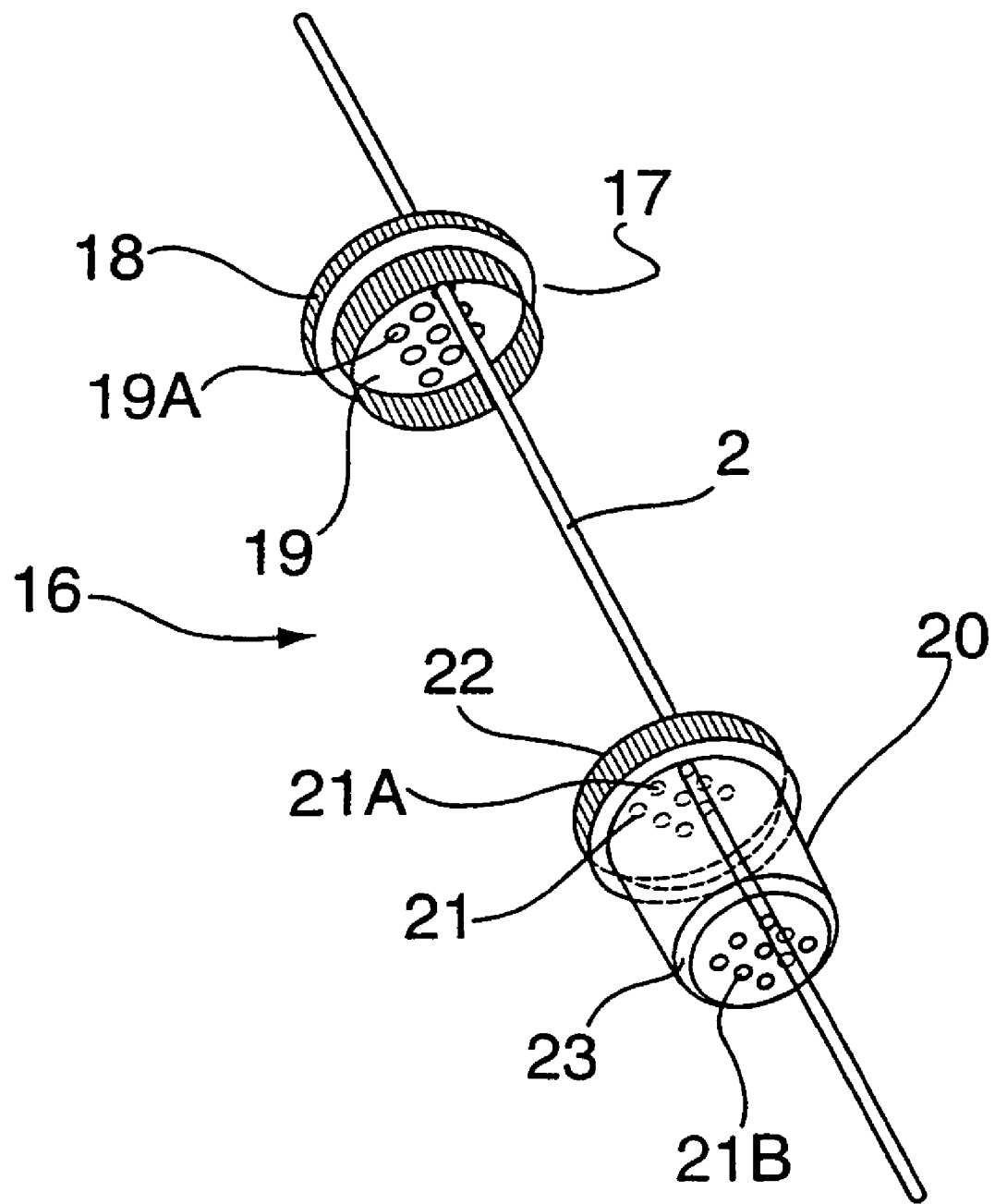
FIG. 3 illustrates a perspective view of a stop bullet and guide bullet in cooperation with the transplantation cannula of FIG. 1.

The bullet guide (16), illustrated in FIG. 3, comprises both a top portion and a bottom portion that are mounted to a stereotactic frame and function as a mechanical guiding system for the transplantation cannula (2). The top portion of the bullet guide (16), comprises a stop bullet (17) and is a hollow cylindrical tube which is closed at its proximal end and circumscribed by a peripheral collar (18). The surface of the closed end embodies a square grid (19) consisting of nine holes (19A) spaced an equidistance apart to one another and sized to accommodate the diameter of the transplantation cannula (2). The bottom portion of the guide (16) is a guide bullet (20), which is a hollow cylindrical tube of similar diameter to the stop bullet (17) but with a longer longitudinal axis. The guide bullet (20) is closed at both the proximal and distal ends and the surface of each end has an identical square grid (21) of holes (21A) and (21B), respectively, to the grid (19) of holes (19A) of the stop bullet (17) to accommodate the insertion of the transplantation cannula (2). Furthermore, the guide bullet (20) is circumscribed by a peripheral collar (22) at its extreme proximal end and has an inwardly bevelled portion (23) with a flat surface at its extreme distal end.

Figure 4:
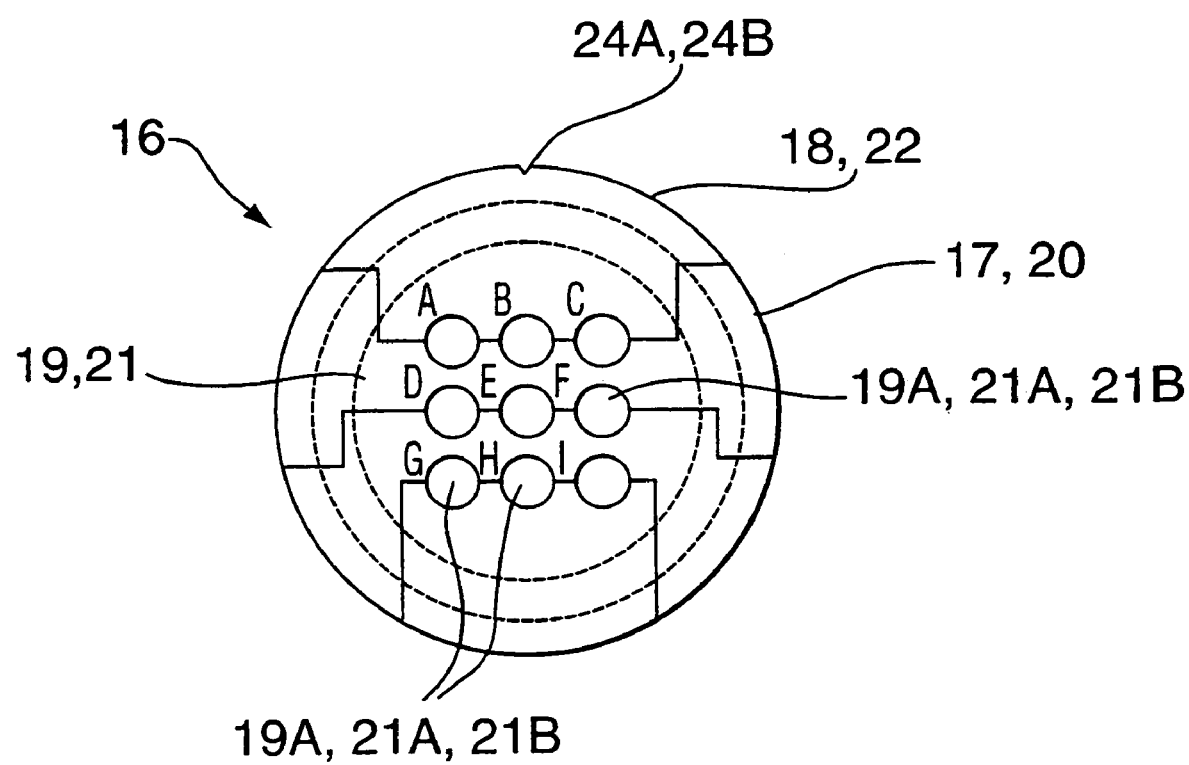
FIG. 4 is an axial view of the stop and guide bullets.

FIG. 4 provides an axial view of the bullet guide (16) showing both the stop bullet (17) and guide bullet (20), and illustrating the square grids, (19) and (21), each consisting of nine holes, (19A), (21A) and (21B), respectively, located equidistantly from one another. Also illustrated is the partitioning of both the stop bullet (17) and guide bullet (20) such that each component can be disassembled into four separate parts to allow for effective cleaning and sterilization. Various different interlocking or interfitting arrangements of parts are also contemplated. Peripheral collars (18) and (22) of the stop bullet (17) and guide bullet (20), respectively, contain indexing grooves, (24A) and (24B), formed of a particular dimension and shape to allow both portions to selectively interface and cooperate with a commercial stereotactic frame when mounted. The positioning of the indexing grooves (24A) and (24B) ensures that when the stop bullet (17) and guide bullet (20) are mounted, their grids, (19) and (21), with holes (19A), (21A) and (21B), will be coaxially aligned one above the other thereby allowing the transplantation cannula to be precisely guided and inserted at a predetermined cerebral target The nine holes (19A) have been individually labelled (A), (B), (C), (D), (E), (F), (G), (H) and (I), and every hole (19A) in the stop bullet (17) lines up with holes (21A) and (21B) of the guide bullet (20). Thus, when the bullets (17) and (20) are correctly aligned coaxially, hole (A) in the stop bullet (17) will be aligned with holes (A) in the guide bullet (20), and so on. Alignment is facilitated by the indexing grooves (24A) and (24B) in the bullets (17) and (20), respectively.

Figure 5:
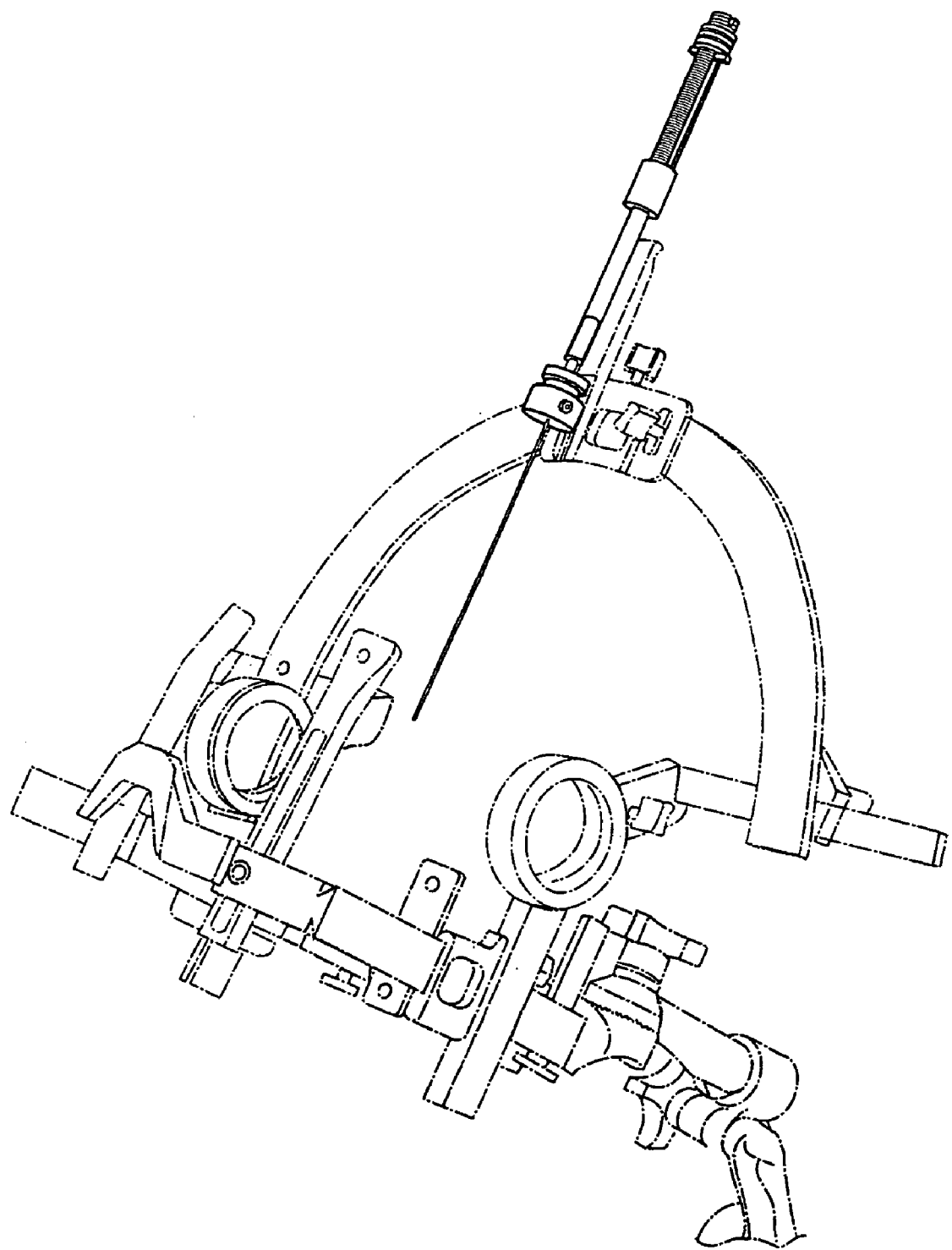
FIG. 5 shows the microinjector and neural transplantation cannula fitted to a stereotactic frame.

FIG. 5 illustrates how the neural transplantation device, comprising the microinjector (1), Hamilton syringe (3) and transplantation cannula (2), and the bullet guide (16) are fitted to a Leksell stereotactic frame (Model A0260-02). When the stop bullet (17) and guide bullet (20) are mounted and coaxially aligned one above the other in a stereotactic frame, the transplantation cannula (2) can be precisely guided and inserted at a predetermined cerebral target.

In the initial stage prior to administration of a cell graft, the plunger (12) of the syringe (3) is in a foremost upward position and the syringe barrel (7) with attached guide nut (8) is in an unwound position inside the plunger guide (5). When an injection is to be administered, the plunger driver (11) is rotated, thereby advancing the syringe plunger (12) in a downward vertical direction through the syringe barrel (7). A specific volume of the cell suspension is subsequently aspirated and deposited through the port holes (15A) and (15B) of the transplantation cannula (2) at the target site. Prior to making a second injection and deposit of the cell suspension, the guide nut (8) is rotated 90° in a clockwise position thereby withdrawing the syringe (3) and cannula (2) in an upward vertical direction at a predetermined distance away from the first target site. Aspiration and delivery of the second volume of cell suspension is made by repeating the operation involving rotation of the plunger driver (11). Sequential repetition of the steps involving rotation of the plunger driver (11) and guide nut (8) to deliver the contents of the syringe (3) and reposition the cannula (2), respectively, allows several injections to be made thereby distributing the cells in a three-dimensional spiral array within the brain tissue.

FIGS. 6A and 6B provide front and top views, respectively, of a sequence of four injections, 3.0 mm apart, made in a single trajectory. The first injection delivers two graft deposits oriented opposite to each other and one at a slightly higher level than the other (solid balls). The cannula (2) is then withdrawn 3.0 mm in a stepwise fashion and rotated 90° clockwise and so that another two deposits can be made (solid balls). The process is repeated two more times until a total of 8 deposits are made per trajectory resulting in a three-dimensional spiral array.

Additional cell deposits at different trajectories are made by removing the microinjector (1) from its operative position, governed by the square grids, (19) and (21), of the bullet guide (16), and then reinserting the transplantation cannula (2) of the microinjector (1) through another specified landmark of holes contained within the grids (19) and (21).

Although only one exemplary embodiment of this invention has been described in detail above, those skilled in the art will readily appreciate that many modifications are possible in the exemplary embodiment without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents, but also equivalent structures.

The following Examples illustrate the invention:

EXAMPLE 1

Animal Studies

Figure 7:
FIG. 7 is a photomicrograph of a coronal section of a rat striatum immunostained with tyrosine hydroxylase (TH) to visualize dopaminergic neurons.

Animals tolerated the transplant procedure well and all of them had surviving grafts 6 to 8 weeks after transplantation. Typically, two graft deposits were observed in the implanted striatum and each graft deposit corresponded to the upper and lower side holes of the transplant cannula (FIG. 7). The cannula tract was clearly visible connecting the upper and lower graft and the deposits appear to be oriented in opposite directions. Numerous TH immunoreactive cells and fibres were observed in the graft deposits and cannula tract (FIG. 7). Fibres were also observed penetrating the host striatum for variable distances and overall the appearance of the grafts was comparable to animals grafted with a glass microcapillary in our laboratory (Mendez et al., *Brain Res.*, 778, pp. 194–204, 1997; Mendez et al., *J. Neurosci.*, 16(22), pp. 7216–7227, 1996). There was no evidence of significant trauma in the grafted area and no tissue disruption was observed in the cannula tract.

EXAMPLE 2

Clinical Studies

Eight patients enrolled in the Halifax Neural Transplantation Program received bilateral putaminal fetal VM tissue obtained from women undergoing elective abortions in the pregnancy termination unit of the Queen Elizabeth II Health Sciences Centre following strict guidelines of a protocol approved by the University and Hospital ethical review boards.

The surgical transplantation procedure was carried out in two stages in which each side was transplanted 4 to 6 weeks apart. Patients were admitted to hospital the night prior to surgery. On the day of surgery, patients were fitted with a Leksell stereotactic headframe under local anaesthesia. The stereotactic coordinates for targets in the putamen were calculated using T1-weighted MRI images and a computerized planning workstation (Surgiplan, Elekta AB, Stockholm, Sweden).

Transplantation was performed with the patient under local anaesthesia and sedation, using a combination of Midazolam (0.25 to 1.0 mg bolus doses) and Proprofol (10 to 20 mg bolus followed by infusion at 15 to 40 mg/kg/min). A burr-hole was placed at the level of the coronal suture and the transplantation cannula was inserted into four different trajectories approximately 3.0 mm apart in the post commissural putamen. A 50 µl Hamilton syringe, fitted with the microinjector, was used to load the 15 µl of cell suspension in the transplantation cannula. The cell suspension was prepared in the same manner as described in the animal experiments. The dead space in the cannula was filled first with medium solution in such a way that the 15 µl of cell suspension was only loaded in the most distal part of the cannula. The cell suspension was deposited along each of the four trajectories previously calculated on the patient's MRI scan. Four injections of approximately 2.5 µl each (eight deposits) were made in each trajectory for a total of 10 µl per trajectory. The injections were made 3.0 mm apart as the cannula was slowly withdrawn in a stepwise fashion and rotated 90° clockwise before each injection at a rate of approximately 1 µl/min (FIGS. 6A and 6B). A wait of 2 minutes was observed between each injection and the cannula was completely withdrawn after 4 minutes from the last injection and the cannula was completely withdrawn after 4 minutes from the last injection. Approximately 4 million cells were deposited in each postcommissural putamen. Patients received 1 g of Ancef intravenously before the skin incision was made and three more doses of 1 g of Ancef intravenously every 8 hours post-operatively. Patients were discharged from the hospital 48 hours after surgery. Patients had an MRI which included T1, T2 and inversion recovery (TR 7000 msec, TE 60 msec and TI 400 msec) sequences in the axial, coronal and sagittal planes 24 hours after surgery to check for target accuracy and bleeding. MRI scans with gadolinium enhancement were also performed at 6 and 12 months after surgery to check for blood-brain-barrier breakdown.

PET scans were performed at the McConnell Brain Imaging Centre (Montreal Neurological Institute, McGill University) before and after the transplant procedure. Scans were performed on the Siemens ECAT HR+ Positron Emission Tomograph in 3D mode, with a resolution of 5 mm FWHM in all directions at the centre of the field of view. Subjects received 5 mCi of [18F]DOPA (FD) as a bolus injection into the antecubital vein over 2 minutes. Their heads were immobilized within the aperture of the PET scanner by a form fitting vacuum device. One hour prior to the scan, subjects received carbidopa, 150 mg p.o. to prevent the peripheral breakdown of FD. On the day of the scan, patients did not receive anti-Parkinsonian medications and they did not eat breakfast prior to the scan. After the injection of FD, PET data was acquired for 90 minutes in 27 time-frames of varying durations.

Figure 8:
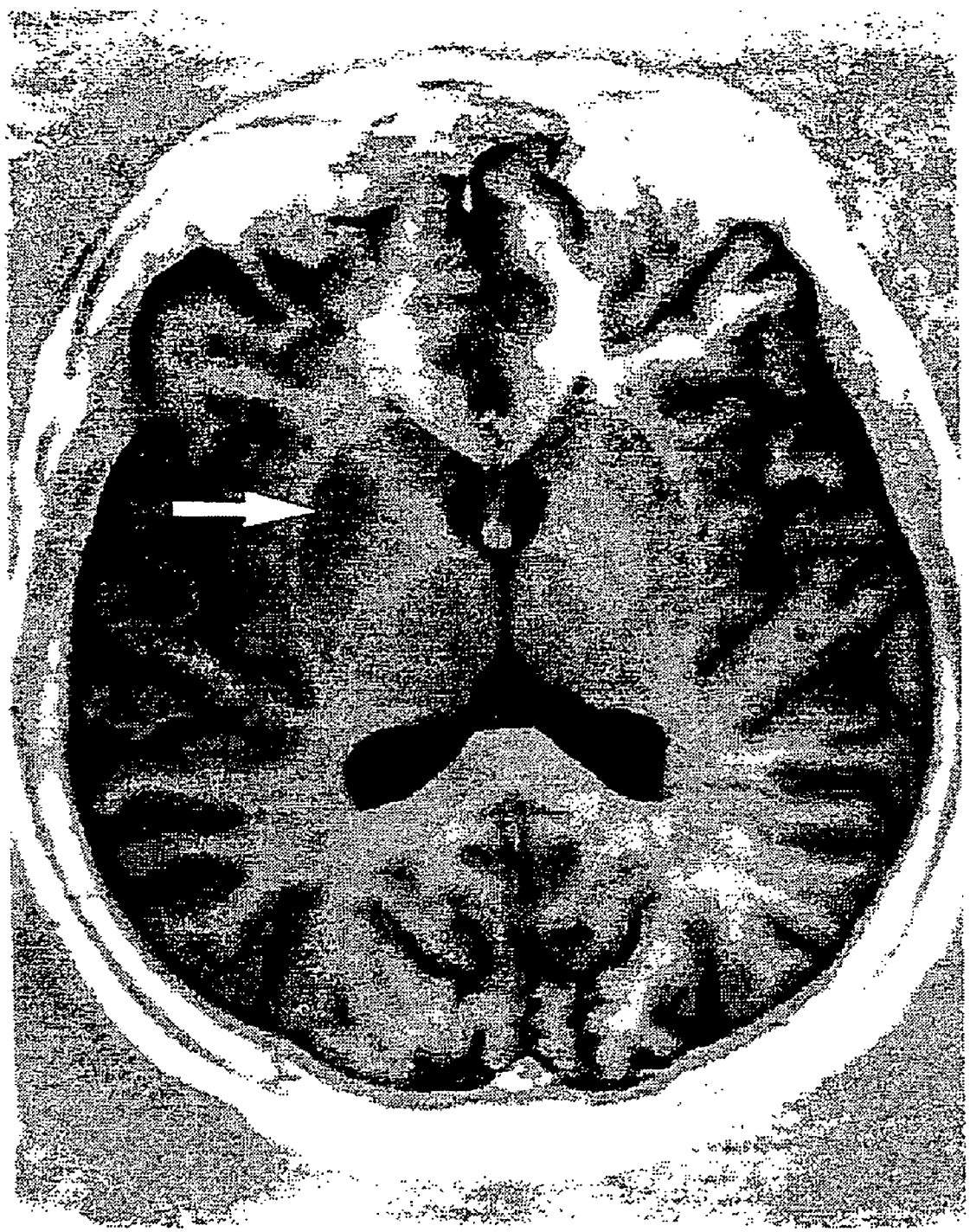
FIG. 8 is a MRI scan (inversion recovery) 24 hours after surgery showing four graft deposits in the right putamen.

A total of 16 transplant operations and 64 trajectories were performed on eight patients with the implantation cannula and microinjector system. The patients tolerated the surgical procedures well and there was no intra-operative or peri-operative complications. The brain MRI scans done 24 hours after surgery showed that the deposits were made in the desired targets in all cases (FIG. 8) and there was no evidence of hemorrhage or tissue damage. The lesioned striatum (left) in FIG. 8 shows the two graft deposits made by the transplant cannula. Note that the orientation of the upper and lower grafts (short arrows) corresponds to the side holes of the cannula. There is no evidence of significant trauma in the transplanted striatum and the grafts are well integrated in the host. The two grafts are connected by the cannula tract and contain TH-positive cells and fibres (long arrow).

The MRI scans with gadolinium enhancement done at 6 and 12 months after transplantation did not show any areas of enhancement which indicates no blood-brain-barrier breakdown.

Figure 9:
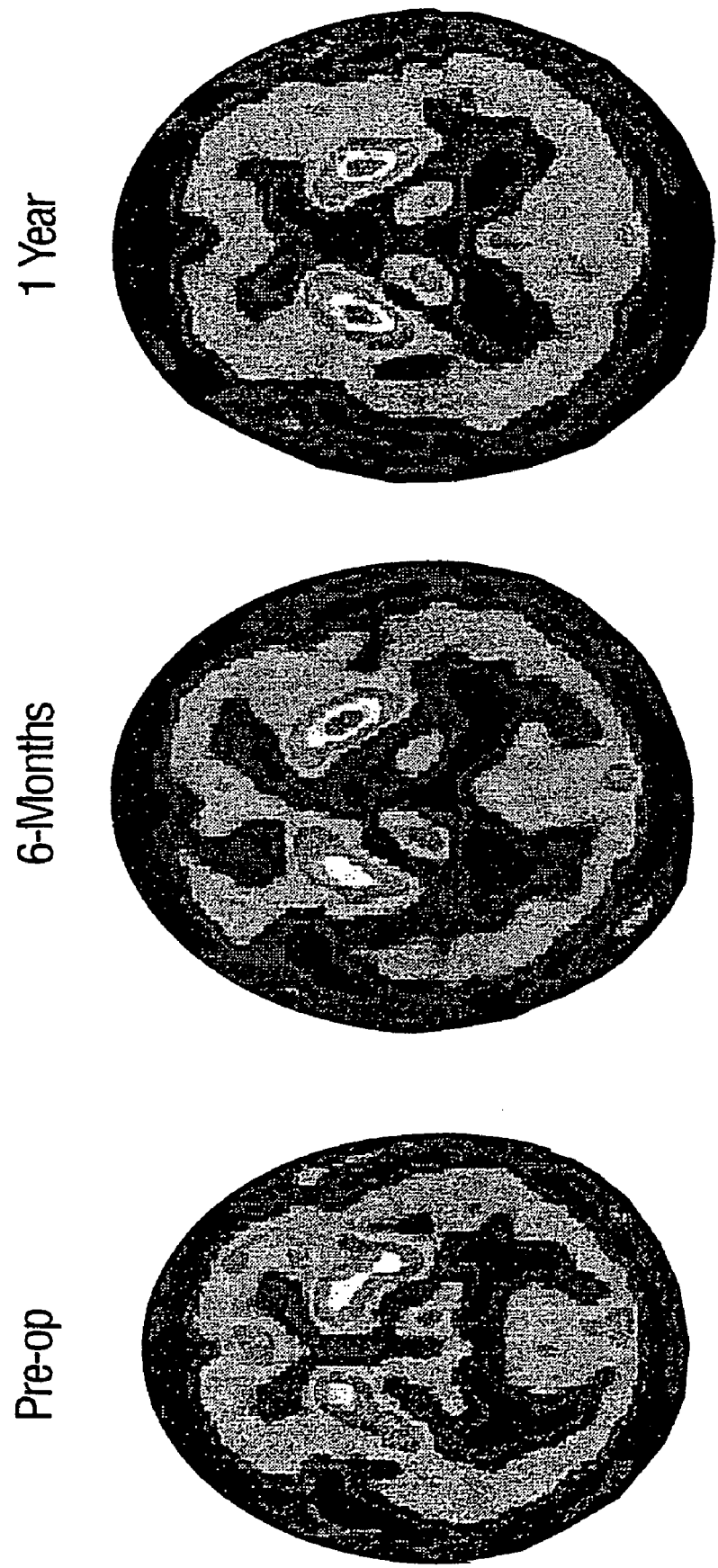
FIG. 9 provides fluorodopa PET scans of a patient transplanted using the microinjector and transplantation cannula.

Post-operative fluorodopa PET scans showed an increase in fluorodopa uptake in the transplanted areas 6 and 12 months after transplantation (FIG. 9). This increase in tracer uptake is an indication of graft survival.

Material and Methods

Implantation Cannula and Microinjector System

The cannula and microinjectory system (FIG. 1) were designed to fit a 50 µl Hamilton syringe and could be adapted to be used with any stereotactic frame system. The Leksell stereotactic frame was used (Model A0260-02, Elekta AB, Stockholm Sweden) (FIG. 5) and the only modification needed was to change the stop and guide to a custom made set with the appropriate diameter for the cannula (0.8 mm). The cannula was manufactured from a stainless steel 21-gauge needle (outer diameter 0.8 mm) and a length of 195 mm. A standard Luer lock was fitted to the proximal end. The cannula tip is rounded and polished to minimize trauma. The proximal end has two side holes (0.3 mm diameter). The first hole is 1.0 mm proximal to the tip and the second hold is 2.0 mm proximal to the first hole but oriented in the opposite direction (FIG. 2).

The microinjector system was manufactured of acetal nylon and ionized aluminum. The microinjector consists of a threaded cylinder with an adapter for the syringe barrel placed distally and a plunger driver proximally (FIG. 1). The syringe plunger is controlled by the plunger driver and can deliver the desired volume of cell suspension accurately.

Animal Experiments

Ten female Wistar rats (Charles River, St. Constant, Quebec, Canada) weighing 200 to 225 g were housed two animals per cage with food and water ad lib and allowed to acclimatize for 7 days in the animal care facility prior to surgery or behavioural testing. All animal procedures were in accordance with the guidelines of the Canadian Council on Animal Care and the University Council on Laboratory Animals. Rats received two stereotactic injections of 6-hydroxydopamine (6-OHDA) into the right ascending mesostriatal dopaminergic pathway under pentobarbital anaesthesia at the following coordinates: (1) 2.5 µl of 6-OHDA (3.6 µg 6-OHDA Hbr/µl in 0.2 µg/µl L-ascorbate 0.9% saline) AP −4.4, L 1.2, DV −7.8, tooth bar −2.4 and (2) 3 µl of 6-OHDA at AP −4.0, L 0.8, DV −8.0, tooth bar +3.4. The injection rate was approximately 1 µl/min. And the cannula was left in place for an additional 4 minutes before slowly being retracted. Following a two-week recovery period in the animal care facility, animals were given an amphetamine challenge (5 mg/kg i.p.) And their rotational scores collected over a 90-minute period. Only animals exhibiting a mean ipsilateral rotation score of nine or more full body turns/ minute were included in the study.

The lesioned rats were transplanted using the clinical cannula and microinjector system. In brief, cell suspensions were prepared from VM of 14-day old rat fetuses and injected stereotactically in the host brains of 6-OHDA lesioned animals. Cell suspensions of fetal VM tissue were prepared by the following procedure. The tissue was incubated in 0.1% trypsin/0.05% DNase/DMEM (Trypsin: Worthington; DNase: Sigma DN-25) at 37° C. for 20 minutes then rinsed four times in 0.05% DNase/DMEM. The tissue was then mechanically dissociated into a "chunky" cell suspension. A final cell concentration of approximately 200,000 cells/µl was used with viability of 98% as determined by the trypan blue dye exclusion method. A total of 500,000 cells (2.5 µl) were implanted into the dopamine-depleted striatum.

Six to eight weeks after transplantation, rats were anaesthetized with an overdose of pentobarbital and perfused transcardially with 100 ml of 0.1 M phosphate buffer, followed by 250 ml of 4% freshly-depolymerized paraformaldehyde in 0.1 M phosphate buffer over 15 minutes. Brains were removed and post-fixed overnight in 4% paraformaldehyde in 0.1 M phosphate buffer before being stored in phosphate-buffered saline containing 30% sucrose for 24 hours. Coronal sections 40 µm thick were cut on a freezing microtome and collected serially in 0.1 M phosphate buffer. Sections were processed for tyrosine hydroxylase (TH) immunohistochemistry using a primary rabbit anti-TH antiserum (1:2,500 Pel Freeze) and the ABC-kit (Vector, Dimension Laboratories).

INDUSTRIAL APPLICABILITY

The neural transplantation system, comprising a microinjector, transplantation cannula and bullet guide in combination with a syringe and mounted to a stereotactic frame, provides a simple, reliable and safe system for improved delivery and maximization of the number of cell graft deposits to a host brain with minimal trauma using a unique spiral technique.

The invention claimed is:

1. A neural transplantation device for use with a syringe (3), including a syringe barrel (7) and plunger (12), said device comprising:

a cannula (2) adapted for connection to a distal end of the syringe barrel (7), said cannula (2) having a single passageway with an open upper end and a lower end defining a blunt closed tip (14) and having a pair of side port holes (15A),(15B) that are diametrically opposed and slightly offset to each other near the vicinity of the cannula tip (14);

a microinjector (1) adapted for connection to a proximal end of a syringe barrel (7) and in cooperation with the syringe plunger (12) for effecting incremental depression of the plunger (12), said microinjector (1) comprising a longitudinal hollow cylindrical sleeve (4) extending into a cylindrical barrel (5) of larger diameter at the distal end thereof, said sleeve (4) capable of receiving a syringe plunger (12), a guide nut (8) rotatably adjustable within the cylindrical barrel (5) and adapted to cooperate with the proximal end of the syringe barrel, (7) and a driver rotatably mounted near the proximal end of the cylindrical sleeve (4) and adapted to cooperate with the syringe plunger (12), whereby operation of the microinjector (1) in combination with the syringe (3) and the cannula (2) allows delivery of an injection such that rotation of the driver renders a downward axial force to the plunger (12) of the syringe (3) thereby forcing contents of the syringe barrel (7) through the side port holes (15A),(15B) of the cannula (2); while rotation of the guide nut (8) in the opposite direction moves the syringe (3) in an upward axial direction to reposition the cannula (2); and rotation of the driver and the guide nut (8) in a repeated manner facilitates sequential delivery of multiple portions of the contents of the syringe barrel (7) along a single trajectory in a three-dimensional spiral array at a predetermined neural injection site; and whereby upon placement of the cannula (2) at a predetermined targeted neural site, the microinjector (1) is capable of effecting incremental depression of the plunger (12) to result in a metered delivery of the contents of the syringe barrel (7) through the cannula port holes (15A),(15B) at the targeted site.

2. The neural transplantation device according to claim 1, characterized in that the guide nut (8) is a small hollow cylindrical spool with a collar (9) at its extreme distal end that acts as a lower boundary stop to limit its position inside the cylindrical barrel (5) when fully wound inside.

3. The neural transplantation device according to claim 2, characterized in that an exterior wall of the guide nut (8) and an interior wall of the cylindrical barrel (5), which receives the guide nut (8), are threaded such that rotation of the guide nut (8) relative to the cylindrical barrel (5) causes a corresponding linear, axial movement of the guide nut (8) through the cylindrical barrel (5).

4. The neural transplantation device according to claim 3, characterized in that the driver comprises a plunger driver (11) and a drive nut (10).

5. The neural transplantation device according to claim 4, characterized in that an exterior wall of the longitudinal cylindrical sleeve (4) and an interior wall of the plunger driver (11) and the drive nut (10) are threaded such that rotation of either the plunger driver (11) or drive nut (10) relative to the cylindrical sleeve (4) causes a corresponding linear, axial movement of the plunger driver (11), drive nut (10), and the syringe plunger (12).

6. The neural transplantation device according to claim 5, characterized in that the cannula (2) has a length sufficient to linearly penetrate and enter a host brain such that the pair of side port holes (15A),(15B) is concurrently positionable at a predetermined targeted site within the host brain.

7. The neural transplantation device according to claim 6, characterized in that the cannula (2) has an outside diameter of about 0.8 mm.

8. The neural transplantation device according to claim 7, characterized in that the side port holes (15A),(15B) are positioned such that the distances between a distal edge of a first (15B) and a second side port hole (15A) to the cannula tip (14) are about 1.0 mm and 3.0 mm, respectively.

9. The neural transplantation device according to claim 8, characterized in that the diameters of the side port holes are the same.

10. The neural transplantation device according to claim 9, characterized in that the diameter of each side port hole (15A),(15B) is 0.3 mm.

11. The neural transplantation device according to claim 10, characterized in that the microinjector (1) is manufactured from acetal nylon and ionized aluminum.

12. The neural transplantation device according to claim 11, characterized in that the cannula (2) is manufactured from stainless steel.

13. A method of using a neural transplantation device defined according to claim 12, for administering an injection, comprising the steps of:

positioning the syringe plunger (12) in an initial upward position;

positioning the syringe barrel (7) with attached guide nut (8) in an essentially unwound position inside the cylindrical barrel (5) of the sleeve (4) of the microinjector (1);

rotating the driver to advance the syringe plunger (12) in a downward axial direction through the syringe barrel (7) thereby aspirating and depositing a portion of the contents of the syringe barrel (7) through the side port holes (15A),(15B) of the cannula (2);

rotating the guide nut (8) to effectively withdraw the syringe (3) and cannula (2) in an upward axial direction at a predetermined distance away from a previous neural target site; and repeating steps involving rotating the driver to deliver a portion of the contents of the syringe barrel (7) and rotating the guide nut (8) to reposition the cannula (2), thereby resulting in sequential delivery of multiple portions of the contents of the syringe barrel (7) in a three-dimensional spiral array per single trajectory at a predetermined neural target site.

14. The method according to claim 13, characterized in that an exterior wall of the longitudinal cylindrical sleeve (4) and an interior wall of the plunger driver (11) and the drive nut (10) are threaded such that rotation of either the drive nut (10) or plunger driver (11) relative to the cylindrical sleeve (4) causes a corresponding linear, axial movement of the drive nut (10), plunger driver (11), and the syringe plunger (12).

15. The neural transplantation device according to claim 1, characterized in that an exterior wall of the guide nut (8) and an interior wall of the cylindrical barrel (5), which receives the guide nut (8), are threaded such that rotation of the guide nut (8) relative to the cylindrical barrel (5) causes a corresponding linear, axial movement of the guide nut (8) through the cylindrical barrel (5).

16. The neural transplantation device according to claim 1, characterized in that the driver comprises a plunger driver (11) and a drive nut (10).

17. The neural transplantation device according to claim 16, characterized in that the plunger driver (11) is adapted to cooperate with the proximal end of the syringe plunger (12) and a distal end of the drive nut (10) is engaged with a proximal end of the plunger driver (11), such that rotation of either the drive nut (10) or plunger driver (11) causes a corresponding linear, axial movement of the drive nut (10), plunger driver (11), and syringe plunger (12).

18. The neural transplantation device according to claim 16, characterized in that an exterior wall of the longitudinal cylindrical sleeve (4) and an interior wall of the plunger driver (11) and the drive nut (10) are threaded such that rotation of either the plunger driver (11) or drive nut (10) relative to the cylindrical sleeve (4) causes a corresponding linear, axial movement of the plunger driver (11), drive nut (10), and the syringe plunger (12).

19. The neural transplantation device according to claim 1, characterized in that the cannula (2) has a length sufficient to linearly penetrate and enter a host brain such that the pair of side port holes (15A),(15B) is concurrently positionable at a predetermined targeted site within the host brain.

20. The neural transplantation device according to claim 1, characterized in that the cannula (2) has an outside diameter of about 0.8 mm.

21. The neural transplantation device according to claim 1, characterized in that the side port holes (15A),(15B) are positioned such that the distances between a distal edge of a first (15B) and a second side port hole (15A) to the cannula tip (14) are about 1.0 mm and 3.0 mm, respectively.

22. The neural transplantation device according to claim 1, characterized in that the diameters of the side port holes are the same.

23. The neural transplantation device according to claim 1, characterized in that the diameter of each side port hole (15A),(15B) is 0.3 mm.

24. The neural transplantation device according to claim 1, characterized in that the microinjector (1) is manufactured from acetal nylon and ionized aluminum.

25. The neural transplantation device according to claim 1, characterized in that the cannula (2) is manufactured from stainless steel.

26. A method of using a neural transplantation device defined according to claim 1 for administering an injection, comprising the steps of:
   positioning the syringe plunger (12) in an initial upward position;
   positioning the syringe barrel (7) with attached guide nut (8) in an essentially unwound position inside the cylindrical barrel (5) of the sleeve (4) of the microinjector (1);
   rotating the driver to advance the syringe plunger (12) in a downward axial direction through the syringe barrel (7) thereby aspirating and depositing a portion of the contents of the syringe barrel (7) through the side port holes (15A),(15B) of the cannula (2);
   rotating the guide nut (8) to effectively withdraw the syringe (3) and cannula (2) in an upward axial direction at a predetermined distance away from a previous neural target site; and
   repeating steps involving rotating the driver to deliver a portion of the contents of the syringe barrel (7) and rotating the guide nut (8) to reposition the cannula (2), thereby resulting in sequential delivery of multiple portions of the contents of the syringe barrel (7) in a three-dimensional spiral array per single trajectory at a predetermined neural target site.

27. The method according to claim 26, characterized in that the driver comprises a plunger driver (11) and a drive nut (10).

28. The method according to claim 27, characterized in that the plunger driver (11) is adapted to cooperate with the proximal end of the syringe plunger (12) and the distal end of the drive nut (10) is engaged with the proximal end of the plunger driver (11), such that rotation of either the drive nut (10) or plunger driver (11) causes a corresponding linear, axial movement of the drive nut (10), plunger driver (11), and syringe plunger (12).

29. The method according to claim 27, characterized in that an exterior wall of the longitudinal cylindrical sleeve (4) and an interior wall of the plunger driver (11) and the drive nut (10) are threaded such that rotation of either the drive nut (10) or plunger driver (11) relative to the cylindrical sleeve (4) causes a corresponding linear, axial movement of the drive nut (10), plunger driver (11), and the syringe plunger (12).

30. The neural transplantation device according to claim 1, characterized in that the driving means comprises a plunger driver (11) and a drive nut (10).

31. A method of using a neural transplantation device defined according to claim 2 for administering an injection, comprising the steps of:
   positioning the syringe plunger (12) in an initial upward position;
   positioning the syringe barrel (7) with attached guide nut (8) in an essentially unwound position inside the cylindrical barrel (5) of the sleeve (4) of the microinjector (1);
   rotating the driving means to advance the syringe plunger (12) in a downward axial direction through the syringe barrel (7) thereby aspirating and depositing a portion of the contents of the syringe barrel (7) through the side port holes (15A),(15B) of the cannula (2);
   rotating the guide nut (8) to effectively withdraw the syringe (3) and cannula (2) in an upward axial direction at a predetermined distance away from a previous neural target site; and
   repeating steps involving rotating the driving means to deliver a portion of the contents of the syringe barrel (7) and rotating the guide nut (8) to reposition the cannula (2), thereby resulting in sequential delivery of multiple portions of the contents of the syringe barrel (7) in a three-dimensional spiral array per single trajectory at a predetermined neural target site.

32. The method according to claim 31, characterized in that the driving means comprises a plunger driver (11) and a drive nut (10).

* * * * *

UNITED STATES PATENT AND TRADEMARK OFFICE
CERTIFICATE OF CORRECTION

PATENT NO. : 7,137,969 B1
APPLICATION NO. : 10/088047
DATED : November 21, 2006
INVENTOR(S) : Mendrez It is certified that error appears in the above-identified patent and that said Letters Patent is hereby corrected as shown below:

<u>Column 2</u>
Line 2, After "et al.," insert -- Nature Medicine, 1 (11), pp. 1189-1194, 1995; Schumacher et --

Signed and Sealed this

Twenty-fourth Day of April, 2007

JON W. DUDAS
*Director of the United States Patent and Trademark Office*